United States Patent
Clampitt

[11] Patent Number: 6,127,187
[45] Date of Patent: Oct. 3, 2000

[54] APPARATUS AND METHOD FOR ANALYZING BLOOD SAMPLES

[76] Inventor: Roger Clampitt, 10 Frithsden, Hemel Hemstead, Hertfordshire, HP1 3DD, United Kingdom

[21] Appl. No.: 09/142,166

[22] PCT Filed: Apr. 1, 1997

[86] PCT No.: PCT/GB97/00909
§ 371 Date: Mar. 31, 1999
§ 102(e) Date: Mar. 31, 1999

[87] PCT Pub. No.: WO97/36163
PCT Pub. Date: Oct. 2, 1997

[30] Foreign Application Priority Data

Mar. 28, 1996 [GB] United Kingdom .................. 9606559

[51] Int. Cl.⁷ .................................................. G01N 33/80
[52] U.S. Cl. .................... 436/70; 436/66; 436/10; 436/45; 436/63; 435/2; 435/7.24; 435/7.25; 422/72; 422/73
[58] Field of Search ................... 436/66, 10, 45, 436/63; 435/2, 7.24, 7.25; 422/72, 73

[56] References Cited

U.S. PATENT DOCUMENTS

| | | | |
|---|---|---|---|
| 4,156,570 | 5/1979 | Wardlaw | 356/36 |
| 4,558,947 | 12/1985 | Wardlaw | 356/39 |
| 5,260,598 | 11/1993 | Brass et al. | 250/574 |
| 5,889,584 | 3/1999 | Wardlaw | 356/39 |

FOREIGN PATENT DOCUMENTS

0142120A2  5/1985  European Pat. Off. .

OTHER PUBLICATIONS

Wardlaw, S.C., and Levine, R.A. Quantitative Buffy Coat Analysis, JAMA (1983) JAMA 249:617–620.

*Primary Examiner*—Jill Warden
*Assistant Examiner*—Huan Tran
*Attorney, Agent, or Firm*—James L. Wilcox

[57] ABSTRACT

Apparatus for analyzing blood or the like has a centrifuge rotor (10) with a means for visibly holding a sample, and a scanning arm (32) which traverses the rotor and includes a means (38) for sending light to the sample to detect the sample component interfaces. A second light source (40) may be provided for colorimetric inspection of the sample.

5 Claims, 3 Drawing Sheets

APPARATUS AND METHOD FOR ANALYZING BLOOD SAMPLES

APPARATUS AND METHOD FOR ANALYSING BLOOD SAMPLES

This invention relates to improved apparatus and method for analysing blood samples.

For analysis and diagnostic purposes it is known to place a sample of blood in a haematocrit tube and thereafter spin the tube on a rotor. The centrifugal force derived from the spinning action causes the various components or phases within the blood sample of different density to separate. Typically the red cells, which are of the highest density within a blood sample, will pack towards one end of the tube. Adjacent to the red cells will be a phase of white blood cells and adjacent to the white blood cells will be a phase of platelets. Further along the tube there may locate plasma of lighter density.

Once the haematocrit tube has been spun separating the various blood components it is known to then determine the percentage content or "count" of each component within the sample. To do this effectively the position of the interface between various phases must be identified with some level of accuracy.

It has been found however that the interface which occurs between the platelets and white blood cells can be hard to detect with a sufficient degree of accuracy. Thus, it is common for operators to estimate the position of the interface between the platelets and the white blood cells by experience or expectation rather than analysis or identification. This estimated percentage is then subtracted from the volume of both the white blood cell and platelet phases to determine the White Blood Cell Count.

The problem with this method is that it does not cater for extraordinary situations or samples. For example, platelets are known to aggregate and by so doing have a greater density which causes the platelets, when the haematocrit tube is spun, to mix with the other blood cells. Thus, when an operator measures the length of the white blood cell and platelet phases, in combination, and thereafter subtracts an estimated platelet volume there can result a sizeable error if there is no significant platelet phase because of the aggregation.

This method of determining the white blood cell count is also generally erroneous or inaccurate when there is an extraordinary high or low platelet content in the blood to be analysed.

It is recognised in the present invention that it would be advantageous if a more accurate method of determining the platelet content could be derived, such that the white blood cell count could also be determined with greater accuracy.

According to the present invention there is a method for obtaining a white blood cell count within a blood sample, the method comprising the steps of:

a) separating the red and white blood cells from the platelets under centrifugal force, but only to such extent that the platelets are suspended in a plasma cloud;

b) optically scanning the platelet cloud to measure the extent of light absorption and or transmission of the cloud;

c) integrating the measurement obtained from step b) above over the length of the platelet cloud to determine the content or mass of platelets in the blood sample;

d) further spinning the sample to such extent that there is an optimum packing of the red cells and white blood cells and there is a clear interface between the red and white blood cells;

e) measuring the volume of the combined packed white blood cell and platelet phases; and f) subtracting the platelet content from the content of white blood cells and platelets in combination to determine the white blood cell count.

Preferably the blood sample is placed in a haematocrit tube which is first spun for approximately 15 seconds at a speed of approximately 10,300 revolutions per minute. This separates the cellular and aqueous components of the blood sample.

Preferably also the optical density of the various phases is determined by measuring the percentage transmission of an optic beam originating from an optical source, such as an infra-red laser, through the sample. Advantageously, this is performed while the centrifuge rotor rotates at a reduced speed of approximately 1000 revolutions per minute, during which a scanning arm holding the optical light source moves across the centrifuge rotor.

Preferably after the content of platelets has been determined the sample is again spun at a circular velocity of approximately 10300 revolutions per minute and for a duration of approximately five minutes to achieve optimum packing and separation of the red and white blood cell phases.

Apparatus which may be used in performing the invention is shown in the accompanying figures, wherein.

Figure 3:
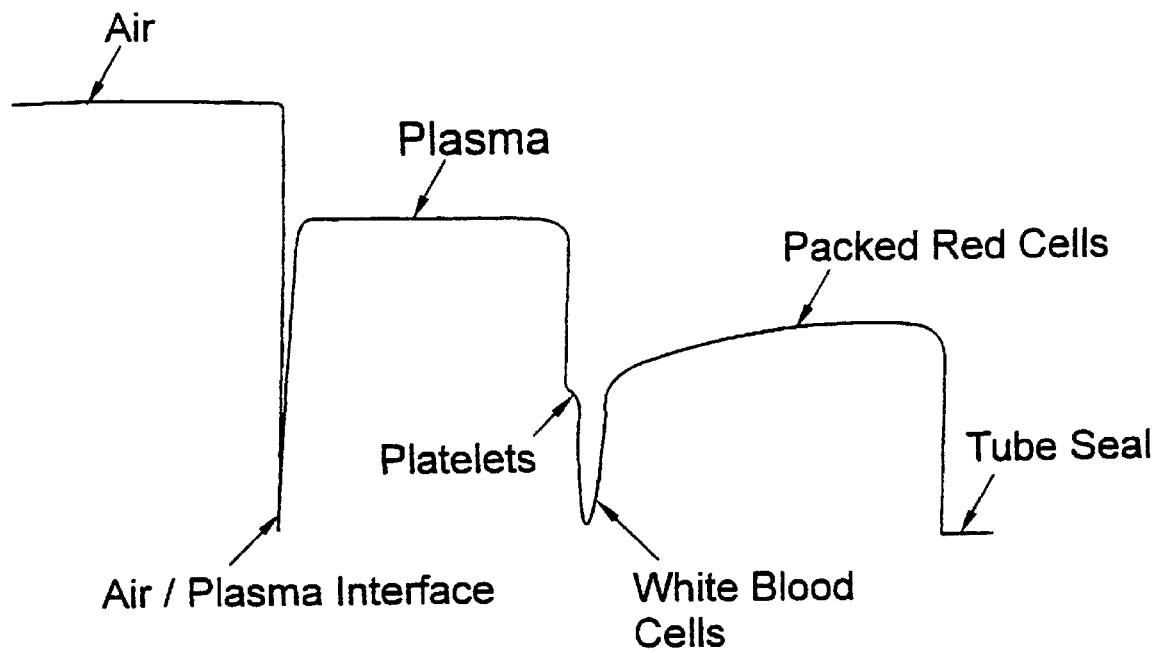

The Figures also include FIG. 3 which shows a typical analogue trace along the length of a haematocrit tube showing the detection and nature of interfaces by the extent of optical transmission through each phase.

Figure 1:
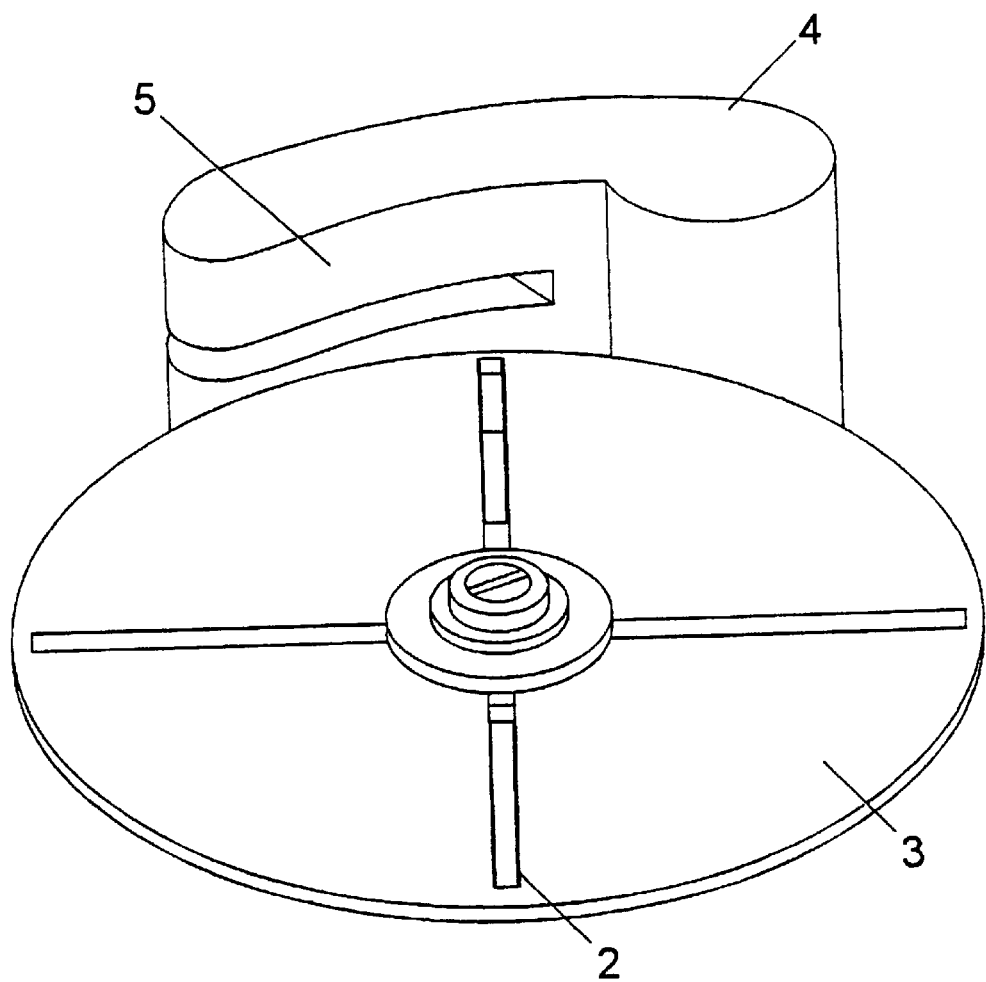
FIG. 1 illustrates a centrifuge and scanning arm.
Figure 2:
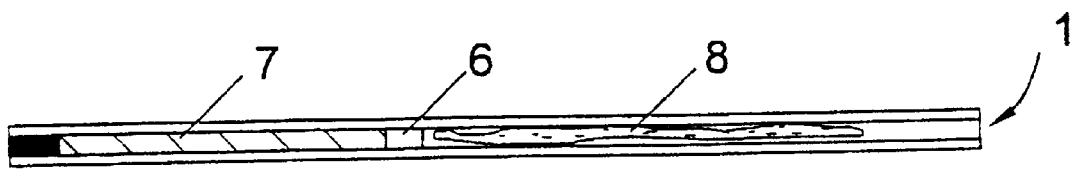
FIGS. 2a and 2b show an haematocrit tube containing a sample of blood wherein the components thereof have been separated to differing extent under centrifugal force.
Figure 2:
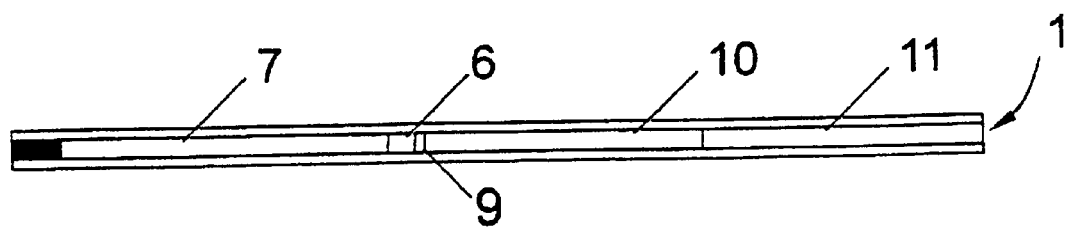

With reference to the Figures, an haematocrit tube 1 as shown in FIG. 2 may be partially filled with a blood sample and then sealed, such as by plugging with a putty, or by heat sealing. The haematocrit tube 1 may then be placed in a groove 2 of the centrifuge rotor 3, illustrated in FIG. 1. The centrifuge is geared and empowered to rotate at a range of speeds up to and in excess of 10,000 revolutions per minute.

Associated with the centrifuge rotor 3 is a scanning arm 4 embodying various optical sources. In particular the scanning arm 4 houses an infra-red laser 5 and a polychromatic visible light source (not shown).

In accordance with the present invention the tube 1 located in the groove 2 is spun at a high speed, such as 10,000 revolutions per minute, but only for a relatively short period of time of say 10 to 20 seconds. Although this does not achieve full packing of the cells it does desirably provide separation of the cellular and aqueous components of the sample, desirably providing the sample to take a form similar to that shown in FIG. 2a. It may be seen in this Figure that the white blood cells 6 and the red blood cells 7 are held at one end of the tube 1, while the platelets are suspended in a plasma cloud 8 toward the other end of the tube 1.

Desirably the centrifuge is then slowed to a speed appropriate for scanning the sample, and if apparatus as shown in FIG. 1 is employed, the scanning arm 4 would then pass over the tube 1 and, in particular, the infrared laser shone through the cloud, enabling the measurement of the transmission of the optical energy through the cloud 8, giving an indication of the cloud's density.

An algorithm relating the density of the cloud 8 to the extent of optical transmission can be used in conjunction with the dimensions of the cloud 8 to determine the percentage of platelets in the sample.

The tube is then spun at the higher velocity again to promote full separation of each cell type and sufficient packing to allow for accurate Packed Cell Volume measurements to be taken. The sample might then be in the form illustrated in FIG. 2*b*. This could be achieved by spinning the tube 1 again at a higher speed of approximately 10 to 10,500 revolutions per minute and for approximately 5 minutes. In FIG. 2*b* the blood sample comprises the following separated components; packed red cells 7, white blood cells 6, platelets 9, plasma 10 and air 11.

FIG. 3 shows an analogue trace of the sample in the haematocrit tube 1 shown in FIG. 2*b*. From an analogue trace it is generally possible to detect the position and nature of the interfaces between the components. However, it is not always clear where the interface is between the platelets 9 and the white blood cells 6. As the invention allows for the relatively accurate determination of the percentage content of platelets in the sample, the dimensions of the white blood cells 6 and platelets 9 can be measured in combination and thereafter the platelet content be subtracted, giving a more reliable white blood cell count than that heretofore possible.

Modifications in the method are possible without departing from the intended scope of the invention, particularly in respect of the techniques, speeds or duration of spinning the sample to achieve the component separation.

What is claimed is:

1. A method for obtaining a white blood cell count within a blood sample, the method comprising the steps of:

a) separating the red and white blood cells from the platelets under centrifugal force, but only to such extent that the platelets are suspended in a plasma cloud;

b) optically scanning the platelet cloud to measure the extent of light absorption and/or transmission of the cloud;

c) integrating the measurement obtained from step b) above over the length of the platelet cloud to determine the content or mass of platelets in the blood sample;

d) further spinning the sample to such extent that there is an optimum packing of the red cells and white blood cells and there is a clear interface between the red and white blood cells;

e) measuring the volume of the combined packed white blood cell and platelet phases; and f) subtracting the platelet content from the content of white blood cells and platelets in combination to determine the white blood cell count.

2. A method as claimed in claim 1 wherein the blood sample is placed in a haematocrit tube which is first spun for approximately 15 seconds at a speed of approximately 10,300 revolutions per minute.

3. A method as claimed in claim 1 or claim 2 wherein the optical density of the platelet cloud is determined by measuring the percentage transmission of an optic beam originating from an optical source through the sample.

4. A method as claimed in claim 3 wherein the optic beam is passed through the sample while the centrifuge rotates at a reduced speed of approximately 1,000 revolutions per minute.

5. A method as claimed claim 1 wherein after the content of platelets has been determined, the sample is again spun at a circular velocity of approximately 10,300 revolutions per minute and for a duration of approximately 5 minutes.

* * * * *